(12) United States Patent
Jagtoyen et al.

(10) Patent No.: US 6,702,875 B2
(45) Date of Patent: Mar. 9, 2004

(54) CARBON FIBER FILTERS FOR AIR FILTRATION

(75) Inventors: Marit Jagtoyen, Lexington, KY (US); Francis John Derbyshire, deceased, late of Lexington, KY (US), by Rosemary Anne Alexander Derbyshire, legal representative (73) Assignee: University of Kentucky Research Foundation, Lexington, KY (US)

( * ) Notice: Subject to any disclaimer, the term of this patent is extended or adjusted under 35 U.S.C. 154(b) by 65 days.

(21) Appl. No.: 09/960,085

(22) Filed: Sep. 21, 2001

(65) Prior Publication Data

US 2003/0089237 A1 May 15, 2003

(51) Int. Cl.⁷ ................................................ B01D 53/04
(52) U.S. Cl. ............................... 95/90; 95/148; 95/276; 95/283; 95/901; 55/527; 422/1
(58) Field of Search ............................. 95/90, 116, 141, 95/148, 273, 274, 276, 283, 901; 55/527; 502/416

(56) References Cited

U.S. PATENT DOCUMENTS

| 3,770,625 A | | 11/1973 | Wallis et al. | |
| 4,828,698 A | | 5/1989 | Jewell et al. | |
| 5,039,651 A | * | 8/1991 | Kosaka et al. | 502/424 |
| 5,308,703 A | * | 5/1994 | Tsujimoto et al. | 428/408 |
| 5,827,355 A | * | 10/1998 | Wilson et al. | 95/114 |
| 5,874,052 A | * | 2/1999 | Holland | 422/171 |
| 5,910,291 A | * | 6/1999 | Skalla et al. | 422/171 |
| 5,912,424 A | * | 6/1999 | Judkins et al. | 95/143 |
| 5,925,168 A | * | 7/1999 | Judkins et al. | 95/27 |
| 5,972,253 A | * | 10/1999 | Kimber | 264/29.7 |
| 5,997,619 A | | 12/1999 | Knuth et al. | |
| 6,063,170 A | | 5/2000 | Deibert | |
| 6,119,689 A | | 9/2000 | Korman | |

FOREIGN PATENT DOCUMENTS

| GB | 2195922 A | * | 4/1988 |
| WO | WO 00/04977 | | 2/2000 |
| WO | WO 00/64578 | * | 11/2000 |

* cited by examiner

*Primary Examiner*—Frank M. Lawrence
(74) *Attorney, Agent, or Firm*—Frost Brown Todd LLC (57) ABSTRACT

Described are filters containing free-activated carbon fibers or activated carbon fibers in the form of a composite used for filtering a variety of contaminants, including pathogens, from air. These filters can provide effective and efficient removal of contaminants from air, requiring only short contact time between the air being filtered and the filter itself, with only a minimum pressure drop across the filter. The characteristics of these filters allow for effective filtration with only thin filter layers being required. The process of filtering air utilizing these filters is also disclosed.

34 Claims, 2 Drawing Sheets

Figure 1

Schematic of test setup for bioaerosol testing of carbon filters

Figure 2

Example of Rapid Heating/Disinfection of Activated Carbon Fiber Composites

Sample weight: 2.83 g, BET surface area 660m$^2$/g
Power applied for 30 second intervals: 390 J
$CO_2$ adsorbed for 150 secs

CARBON FIBER FILTERS FOR AIR FILTRATION

TECHNICAL FIELD

The present invention relates to filters capable of removing a variety of contaminants, including pathogens, from air by filtration. The filters provide effective filtration of a broad range of contaminants at high flow rates with relatively low pressure drops. In particular, the invention encompasses filters that comprise activated carbon fibers, particularly activated carbon fiber composites, for removing a broad spectrum of contaminants, including viruses, from air. Additionally, the invention relates to a method of removing contaminants from air using those filters.

BACKGROUND OF THE INVENTION

The purity of the air we breathe is critical to our health and well being. Yet, that air contains a very broad range of contaminants including, for example, particulates, harmful chemicals, organic materials, and microbiological organisms, such as bacteria, parasites, protozoa and viruses. In addition to the health needs of the general public, specific situations, such as factory floors, public waiting areas, medical and surgical suites, hospital rooms, manufacturing operations (such as for the manufacture of certain electronic components), and airplane cabins, offer particularly difficult and challenging requirements for air purification and filtration systems.

While air filtration devices have been developed to address at least some of these needs, they tend to require a trade-off between filtration efficacy/efficiency and the large, cumbersome and complex nature of the device, i.e., greater efficacy/efficiency generally requires greater complexity. Further, devices which are used to filter out particularly small components, such as biological components, because they frequently rely on very small pore size, tend to require low flow rates or have high pressure drops, thereby rendering the systems relatively inefficient. Examples of some of these prior art systems are described below.

U.S. Pat. No. 3,770,625, Wallis, et al., issued Nov. 6, 1973, describes the use of activated carbon treated with sodium hydroxide to remove viruses from fluids, such as waste water.

U.S. Pat. No. 4,828,698, Jewell, et al., issued May 9, 1989, describes a cylindrical filter having multiple separate components made from polypropylene microfibers for removing particulates, chemicals and pathogens from liquids. These filters are said to provide good flow rates during the filtration process.

U.S. Pat. No. 5,997,619, Knuth, et al., issued Dec. 7, 1999, describes an air filtration system which includes HEPA filters to remove particulates and ultraviolet irradiation to provide a germicidal effect to the filtered air.

U.S. Pat. No. 6,063,170, Deibert, issued May 16, 2000, describes an air filtration system, which includes four separate units: a prefilter to remove dust particulates, germicidal UV lamps to remove bacteria, a medicated wet filtration system for viruses, and a final carbon filter.

U.S. Pat. No. 6,119,689, Korman, issued Sep. 19, 2000, describes a personal air filtration system which uses a combination of HEPA and ULPA filters sandwiching an electrostatic filter. The system is primarily aimed at filtering out particulate materials.

There is a need for a simple filter capable of simultaneously removing a broad spectrum of contaminants from air. This filter would comprise a single small, lightweight, self-contained system rather than a complex multi-component and/or multi-stage system to remove the various contaminants. Such a filter would not only be more reliable than a complex system, but it would also be far more portable and economical. In addition, it would be efficient in its use, permitting a relatively high flow rate through the filter, as well as exhibiting a relatively low pressure drop through the filter system. This would enable the filter not only to be adopted for home use, but also in a variety of situations, such as in a factory and manufacturing context, medical and surgical contexts, and areas where large numbers of people are together for relatively long periods of time, such as hospital or doctor waiting rooms and airplane cabins. The filters of the present invention meet these needs.

Although PCT Published Application No. WO 00/04977, Jagtoyen, et al., published Feb. 3, 2000, describes carbon filters which are used to remove a variety of contaminants, including pathogens, from fluids, that application does not disclose the air filtration filters and methods of the present application, and particularly does not disclose the relatively high flow rates and the relatively small filtration paths which provide outstanding filtration of air utilizing the present invention.

SUMMARY OF THE INVENTION

The present invention relates to a process for removing contaminants, including for example, organic materials and pathogens, from air, comprising passing said air, at a flow rate of from about 3 to about 30 lpm, through a filter comprising an activated carbon fiber composite, said filter having a density of from about 0.35 to about 0.70 g/cc. Preferred filters utilized in this process have a burn-off during activation of at least about 20% and no greater than about 70%, particularly from about 40% to about 50%. Preferred filter shapes are disc filters, candle/annular filters, corrugated filters or block filters. These composite filters, when compared to an analogous filter utilizing free fibers, can provide excellent filtration of a variety of contaminants at higher flow rates and with lower pressure drops.

The present invention also encompasses a filter for removing contaminants, including for example, organic materials and pathogens, from air, comprising activated carbon fibers (preferably in the form of a composite), said filter having a density of from about 0.35 to about 0.70 g/cc, and at least one wall of said filter having a thickness of no greater than about 3 inches (preferably no greater than about 2 inches, most preferably no greater than about 1 inch), through which at least a portion of the air passes during the filtration process. Preferred filters have a burn-off during activation of at least about 20% and no greater than about 70%, most preferably between about 40% and about 50%. These filters preferably have a structure of a disc filter, a candle/annular filter, a corrugated filter, or a block filter. The filters are able to filter air effectively (removing a broad range of contaminants) through a relatively thin wall thereby allowing a higher flow rate and a lower pressure drop than other types of air filters.

Finally, the present invention encompasses a process for removing contaminants, including for example, organic materials and pathogens, from air, comprising passing said air through a filter comprising activated carbon fibers (preferably in the form of a composite), said filter having a density of from about 0.35 to about 0.70 g/cc, such that at least a portion of the air passes through a wall in said filter having a thickness of no greater than about 3 inches (preferably no greater than about 2 inches, most preferably no greater than about 1 inch).

DETAILED DESCRIPTION OF THE INVENTION

As used herein, an "activated carbon fiber" means activated carbon in a form having a relatively high aspect ratio (i.e., ratio of length to diameter). In general, an aspect ratio of at least about 2:1 is preferred, with a ratio of at least about 4:1 being especially preferred. Smaller ratios can sometimes be used in which case the carbon is termed an "activated carbon particulate" which normally has an aspect ratio of about 1:1. The smaller the aspect ratio, the higher the density and pressure drop of the composite will be.

As used herein, an "activated carbon fiber composite" means that activated carbon fibers or particulates are bound together using a binder. Such binders include resins, other polymers, pitches, epoxy resins, adhesives and coal powders, as well as others well known in the art, including phenolic resins. These binders can be introduced in a fluid medium, as well as by solids mixing. An activated carbon fiber composite will be monolithic and, in that way, may provide post-processing handling benefits relative to free fibers.

As used herein, a "filter" is any article of manufacture containing activated carbon fibers and/or particulates to enable their function in removing contaminants, such as organic materials and pathogens, from air. Such a filter may be as simple as the fibers and an enclosure means to retain the fibers. When the filter comprises free fibers that are not bound together in the form of a composite, it is apparent that such an enclosure must be capable of preventing loss of fibers during operation, as well as maintaining the desired inter-fiber network during use. Several representative embodiments for the filter of the present invention are described below. Also as used herein, the terms "filters" and "filtration" refer to removal mechanisms, including those with respect to pathogen removal, via either or both adsorption and size exclusion. Thus, these terms do not refer to mechanisms that merely "kill" pathogens (e.g., heating, chemical treatment, or UV treatment). While the present filters are effective in terms of removing pathogens from the air, without requiring the use of materials that kill the pathogens, it will be recognized that it may be desirable in certain circumstances to include in the filters, for example, chemical treatments that aid in the purification of the air source. This could, for example, have applications for adsorption of chemical warfare agents such as CNCl and others.

The chemical treatment could include incorporation of certain functional groups on the carbon surfaces that attract viruses and bacteria or the incorporation of metals on the carbons. Metal impregnation of filters, i.e., with Cu, Co, Ni, Ag, or Fe can be used to enhance the adsorptive capacity for certain chemical and biological warfare agents.

Figure 2:
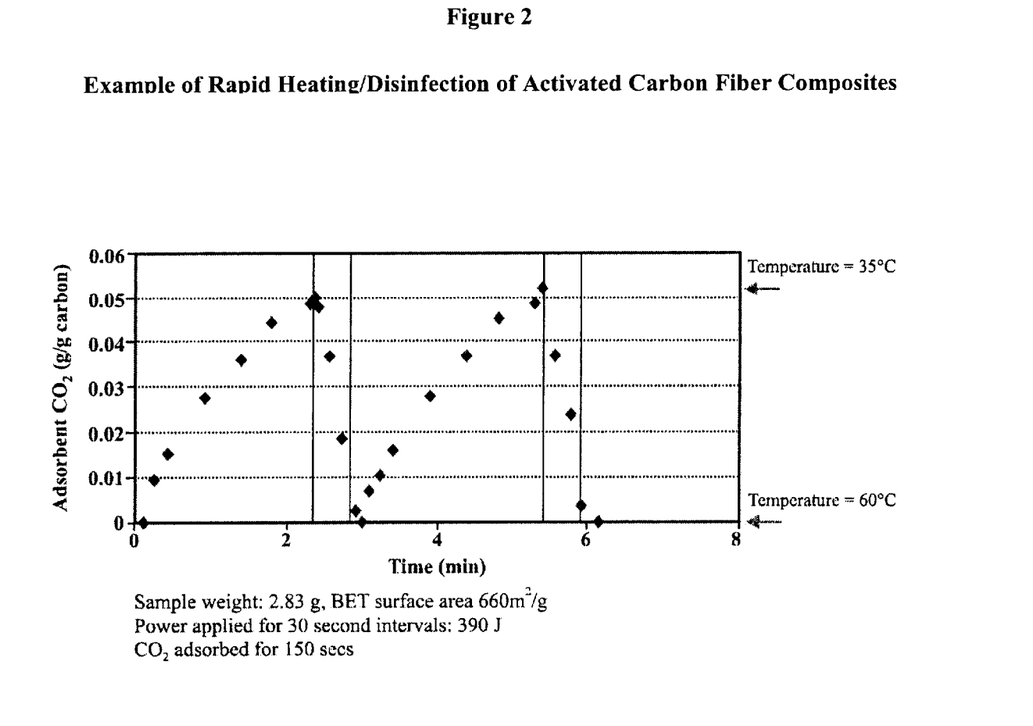
FIG. 2 is an example of the rapid heating/disinfecting properties of the activated carbon fiber composites of the present invention.

The activated carbon filters can be disinfected and regenerated in-situ by rapidly heating them to at least about 60° C., preferably at least about 100° C., while they are off-line. This could be achieved by using two separate activated carbon filters in the adsorption unit. When one unit has been on line for a certain amount of time, the gas flow is switched to the other filter while a current is passed through the contaminated filter to heat it to 100° C. for a few minutes to disinfect it and prevent growth of bacteria/viruses. This is particularly important in applications where the filters treat air in hospitals, surgery suites and for biological warfare, such as adsorption of anthrax. This is a safe way to remove biological contaminants and destroy them in situ without a human being having to handle the filter. The composites have some internal resistivity which allows rapid heating when a current is applied. An example of a heating cycle is shown in FIG. 2. In this experiment $CO_2$ was adsorbed on the filter for 150 seconds. Then, a current was turned on for 30 seconds, rapidly increasing the temperature from 30° to 60° C. in 30 seconds.

As used herein, the term "free fibers" means that the individual activated carbon fibers are not bonded together by the use of a binder. The avoidance of employing such a binder may facilitate production of the filter in that there may be fewer processing steps and less energy consumption involved.

As used herein, the terms "microorganism", "microbiological organism" and "pathogen" are used interchangeably. These terms refer to various types of microorganisms that can be characterized as bacteria, viruses, parasites, protozoa and germs.

Other terms used herein are defined in the specification where discussed.

The filters of the present invention comprise activated carbon fibers and/or particulates, such that the filter is capable of removing from air at least about 99% of viruses. That is, the filter has a Virus Removal Index (VRI) of at least about 99%. Preferably, the filter has a VRI of at least about 99.9%, more preferably at least about 99.99%, even more preferably at least about 99.999%, and still more preferably at least about 99.9999%. In addition to this VRI capability, the filters are also preferably capable of removing at least about 99.999% of bacteria (i.e., the filter will have a Bacteria Removal Index (BRI) of at least about 99.999%). Furthermore, the filter preferably will be capable of removing at least about 99.9% of parasites and protozoa (i.e., the filter has a Parasite Removal Index (PRI) of at least about 99.9%). Preferably, the filter has a PRI of at least about 99.99%, and more preferably at least about 99.999%. Finally, the filters are effective in removing particulates and organic materials from the air.

Activated Carbon Fibers

Carbon fibers are produced commercially from rayon, phenolics, polyacrylonitrile (PAN), or pitch. The pitch type is further divided into fiber produced from isotropic pitch precursors, and those derived from pitch that has been pretreated to introduce a high concentration of carbonaceous mesophase. High performance fibers, i.e., those with high strength or stiffness, are generally produced from PAN or mesophase pitches. Lower performance, general purpose fibers are produced from isotropic pitch precursors. The general purpose fibers are produced as short, blown fibers (rather than continuous filaments) from precursors such as ethylene cracker tar, coal-tar pitch and petroleum pitch prepared from decant oils produced by fluidized catalytic cracking. Applications of isotropic fibers include: friction materials; reinforcements for engineering plastics; electrically-conductive fillers for polymers; filter media; paper and panels; hybrid yards; and as a reinforcement for concrete. More recently, interest has developed in activated forms of isotropic carbon fibers, where high surface areas can be produced by partial gasification in steam or other oxidizing gases. Activated carbon fibers have novel properties that make them more attractive than conventional forms (powders or large size carbons) for certain applications. While porosity can be generated in most types of carbon fibers, low modulus fibers produced from isotropic pitch are particularly suited for activation because of their unique structure, where the random packing of small crystallites allows the development of an extensive pore structure.

Activated carbon fibers can be characterized by their length, diameter, porosity, specific surface area, and elemental composition. Length is meant to describe the distance from end to end of a fiber. The diameter refers to the mean diameter of a fiber. Porosity is characterized by the mean pore volume within the fiber. Specific surface area is a measure of the fiber surface area, including the area within the pores, per unit of mass of fiber. For the present invention, activated carbon fibers will preferably have: specific surface areas in a range of from about 100 to about 4,000 $m^2/g$, more preferably from about 500 to about 3,000 $m^2/g$, still more preferably from about 1,000 to about 2,500 $m^2/g$; diameters in a range of from about 5 to about 50 $\mu$m, more preferably from about 10 to about 25 $\mu$m, still more preferably from about 15 to about 20 $\mu$m; and mean pore sizes from about 2.5 Å to about 300 nm, more preferably from about 5 Å to about 200 nm, still more preferably from about 10 Å to about 100 nm. The fibers can be solid or hollow. Activated carbon fibers have a narrow, submicron range of surface features not found in other activated carbon forms such as granules, powders, pellets, or other irregular shapes impregnated with carbon.

The manufacture of activated carbon fibers is described thoroughly in the literature and such fibers are available commercially from several sources. As discussed, in general, carbonized fibers are made by carbonizing polyacrylonitrile (PAN), phenol resin, pitch, cellulose fiber or other fibrous carbon surfaces in an inert atmosphere. The raw materials from which the starting fibers are formed are varied, and include pitch prepared from residual oil from crude oil distillation, residual oil from naphtha cracking, ethylene bottom oil, liquefied coal oil or coal tar by treatment such as filtration, purification, distillation, hydrogenation or catalytic cracking. The starting fibers may be formed by various methods, including melt spinning and melt blowing. Carbonization and activation provide fibers having higher surface areas. For example, activated carbon fibers produced from petroleum pitch are commercially available from Anshan East Asia Carbon Fibers Company, Inc. (Anshan, China) as Carboflex® pitch-based activated carbon fiber materials, and Osaka Gas Chemicals Company, Ltd. (Osaka, Japan) as Renoves A® series—AD'ALL activated carbon fibers. The starting materials are a heavy petroleum fraction from catalytic cracking and a coal tar pitch, respectively, both of which must be purified to remove fines, ash and other impurities. Pitch is produced by distillation, thermal cracking, solvent extraction or combined methods. Anshan's Carboflex® pitch-based activated carbon fiber materials are 20 $\mu$m in diameter with a specific surface area of about 1,000 $m^2/g$. They come in various lengths including:

P-100 milled-activated carbon fibers; 100 $\mu$m length
P-200 milled-activated carbon fibers; 200 $\mu$m length
P-400 milled-activated carbon fibers; 400 $\mu$m length
P-600T milled-activated carbon fibers; 600 $\mu$m length
P-3200 milled-activated carbon fibers; 3.2 mm length
C-6 chopped activated carbon fibers; 6 mm length Osaka Gas Chemicals Renoves® Series—AD'ALL activated carbon fibers are 18 $\mu$m in diameter with various specific surface areas ranging from 1,000 to 2,500 $m^2/g$. They come in various lengths, including the following (the specific surface areas are noted parenthetically):

A15 milled AD'ALL activated carbon fibers; 700 $\mu$m length (1,500 $m^2/g$)
A20 milled AD'ALL activated carbon fibers; 700 $\mu$m length (2,000 $m^2/g$)
A15 chopped AD'ALL activated carbon fibers; 6 mm length (1,500 $m^2/g$)
A20 chopped AD'ALL activated carbon fibers; 6 mm length (2,000 $m^2/g$)
A10 random length AD'ALL activated carbon fibers; random lengths (1,000 $m^2/g$)
A15 random length AD'ALL activated carbon fibers; random lengths (1,500 $m^2/g$)
A20 random length AD'ALL activated carbon fibers; random lengths (2,000 $m^2/g$)
A25 random length AD'ALL activated carbon fibers; random lengths (2,500 $m^2/g$)

Applicants believe that certain physical properties common to both the composite and noncomposite structures described herein provide the surprising pathogen removal properties of the present invention. For example, bulk density is commonly used in the art to describe carbon containing structures. The filters of the present invention will have a bulk density of from about 0.35 to about 0.7 $g/cm^3$, preferably from about 0.35 to about 0.5 $g/cm^3$, still more preferably about 0.35 to about 0.4 $g/cm^3$. In having calculated the bulk density and knowing the dimensions of the activated carbon fiber, one can determine the average interstitial spacing between fibers. It is discovered that interstitial spacing between fibers (also called inter-fiber spacing) is the critical parameter which controls the removal of microorganisms. Optimal interstitial spacing is achieved when the activated carbon fibers are compressed along the longitudinal or flow axis of the filter.

While not wishing to be bound by theory, applicants believe that the surprising ability of the present filters to remove small pathogens, particularly viruses, is due to the: 1) inter-fiber spacing that results from the packing of the activated carbon fibers, and the resulting flow mechanics conditions; and 2) fast adsorption kinetics and large adsorption capacity exhibited by the activated carbon fibers, when compared to granular or powder activated carbon. It is believed that the initial attachment of microorganisms, in particular bacteria and viruses, onto the activated carbon fibers is governed by the following interactions: 1) classical long-range colloidal (DLVO) and Lewis acid-base (AB); 2) short-range surface polymer and appendage; and 3) strong short-range (i.e., 0.1 to 0.2 nm).

The classical long-range DLVO colloidal forces include the electrostatic (EL) and van der Waals (vdW) dispersion, and depend on the surface characteristics of the microorganisms and fibers, and the distance between them. The electrostatic and vdW forces are applicable at separation distances above 2 nm. Below 2 nm, the AB forces (i.e., electron-donor/electron-acceptor interactions) are dominant. Note that the AB forces include the typical hydrophobic forces. The surface polymer interactions are based on the fact that the microorganisms contain polymers (e.g., lipopolysaccharides (LPS), extracellular polysaccharides (EPS), and surface proteins in Gram-negative bacteria; and proteins in viruses) and appendages (e.g., fimbriae in bacteria) in their outer shells. Finally, the strong short range forces are based on chemical bonds, such as covalent (i.e., strong bonds with a requirement of about 40 to 200 kT to break) and hydrogen bonds (i.e., weaker bonds with a requirement of about 4 to 16 kT to break).

Some of the above forces are attractive and the rest are repulsive. For example, the electrostatic forces are typically repulsive, since most of the surfaces are negatively charged (except for modified surfaces as well as some unmodified clay structures and asbestos). The vdW dispersion forces are typically attractive, whereas the AB forces can be either attractive or repulsive. Similarly, the surface polymer interactions can be either attractive, when the polymers have high affinity (i.e., adsorb) for the carbon fiber surface, or repulsive, when the surface polymers interact sterically with the carbon fiber surface.

According to the DLVO-AB model, adhesion of microorganisms onto carbon fiber surfaces is possible in an attractive primary (irreversible) or secondary (typically reversible) energy minimum. A typical secondary minimum occurs at separation distances on the order of 10 nm, and includes an energy well of about 5 kT.

The above described initial attachment is followed by subsequent steps that improve the attachment and are based on the excretion of various polymeric substances (e.g. extracellular polysaccharides—EPS) by bacteria during their metabolic cycle. This excretion is believed to cause strengthening of the attachment as well as an increase in the attachment sites for microorganisms that follow them. Furthermore, fast adsorption of large quantity of nutrients by the activated carbon fibers facilitates the adsorption of microorganisms, as the latter are seeking nutrient-rich environments.

In terms of the mechanics of the flow of pathogens in the filter, it is believed that the distance between two adjacent fibers, c, is critical in achieving attachment of pathogen to the fibers. In general, pathogens might flow close to the surface of a fiber so that the overall attractive force would cause them to attach to the surface. On the other hand, pathogens might flow far away from the fiber surface so that the overall attractive force cannot "pull" them towards the fiber surface for attachment.

In terms of the effect of the inter-fiber distance (also called spacing) on pathogen attachment onto the fiber surfaces, it is believed that there is an optimum range of inter-fiber distances that is necessary for pathogen attachment to fibers and removal from water. When this inter-fiber distance c is relatively large, then the majority of pathogens do not come close to the fiber surface for the forces mentioned above to cause attachment to the surfaces. As a result, the majority of pathogens do not get removed from the incoming air stream. On the other hand, when this inter-fiber distance is relatively small, then the majority of pathogens come close to the surface of the fibers and experience the forces mentioned above. However, the shear conditions at these small gaps are high, and it is expected that the shear forces are high enough to overcome the attractive forces between pathogen and carbon surfaces. In these conditions there might be some pathogens that do get attached to the fibers. However, it is expected that due to high shear forces these pathogens might experience dislodging at some later point in time. As a result, the majority of pathogens do not get removed from the incoming air stream. Therefore, there is an optimum range of inter-fiber spacing that strikes a balance between shear forces, attractive and repulsive forces. This balance ensures that pathogens get removed during their flow in the carbon fiber filters.

Finally, the fast adsorption kinetics and large adsorption capacity exhibited by the activated carbon fibers has been shown to exist for various chemicals, such as benzene, chlorine, toluene, acetates etc. However, it has not been shown before that such characteristics of the activated carbon fibers are applicable to microorganisms and in particular to viruses.

In its first aspect, the filters of the present invention comprise an activated carbon fiber and/or carbon particulate composite which is prepared in accordance with methods known in the art. For example, such methods of binding activated carbon fibers together include the use of resins, other polymers, pitches, epoxy resins, adhesives and coal powders, as well as others well known in the art, including phenolic resins. These binders can be introduced in a fluid medium as well as by solids mixing. Thus, in one embodiment a selected carbon fiber is prepared to a given average length and is mixed in a water slurry with a carbonizable organic powder. The desired monolithic configuration is then molded from the slurry. The resulting green form is dried and removed from the mold. The composite is then cured and carbonized under an inert gas. Once carbonized, the composite is readily machined to the final desired dimensions. The composite material is activated to develop the pore structure of the fibers before or after machining. Another option is to use preactivated fibers and to form, cure and optionally carbonize, and further optionally subject the filter to mild secondary activation to produce the final product.

A carbon composite filter of the present invention includes a composite of carbon fibers and/or particulates and binder having a cured density prior to activation of from about 0.25 to about 0.85 g/cc, more preferably from about 0.3 to about 0.75 g/cm; an activated density following activation of from about 0.35 to about 0.70 g/cm, more preferably from about 0.35 to about 0.50 g/cm; and a burn-off off during activation of at least about 20%, at most up to about 70%, and preferably between about 40% and about 50%. Still more preferably, the composite has a void volume of from about 63% to about 95%, preferably from about 71% to about 81%; as well as a mean interfiber spacing of from about 30 $\mu$m to about 302 $\mu$m, more preferably from about 42 $\mu$m to about 73 $\mu$m. In general, higher densities provide better removal of contaminants and densities greater than the stated ranges used. However, the defined ranges are preferred since they provide acceptable pressure drops.

Still more specifically, the carbon fibers in the activated fiber composite block are characterized by a micropore volume of from about 0.2 to about 0.9 cc/g, more preferably from 0.3 to 0.8 cc/g; and a BET surface area of from about 500 to about 3,000 $m^2/g$, more preferably from about 800 to about 1,600 $m^2/g$.

An activated carbon fiber composite material having a rigid, open, monolithic structure with a high permeability, and good control over the composite's overall porosity, may be made in the following manner. The composite of the present invention is comprised generally of carbon fibers and a binder. The composite is strong and permeable, allowing air to easily flow through the material. At the same time, when activated, the carbon fibers provide a porous structure of adsorption. Synthesis of the carbon fiber composites generally comprises mixing a selected carbon fiber and a binder, for example, a carbonizable organic powder such as a phenolic resin, with water to form a slurry. The desired monolith configuration is molded from this slurry. The resulting green form is dried and removed from the mold. The composite is cured prior to carbonization under an inert gas. The composite material is then activated to develop the porous structure of the fibers. Alternatively, carbonization and activation may be completed in a single step. A composite may be readily machined to the desired final configuration either before or after activation. Composites can be made from preactivated fibers, so that no or less activation may be necessary after forming.

The filters of the present invention may take on any of the shapes commonly used for air filtration systems. However, one of the benefits of the present invention is that relatively thin layers of the activated carbon composites (or free fibers) can be used to achieve both good flow rates of the air through the filter, and effective filtration of the air. Thus, preferred shapes for the filters of the present invention include disk shape filters, candle shape filters, (i.e., an annular ring of filter material), corrugated shape filters and block shape filters. Such filters should include at least one wall, through which the air passes during the filtration process, having a thickness of no greater than about 3 inches, preferably no greater than about 2 inches, most preferably, no greater than about 1 inch. Thus, for example, the thickness of a disk filter (with the air flow passing through that thickness) of the present invention could be about 1 inch or less. It is this ability to utilize such thin filters, thereby providing excellent flow rates and small pressure drops, without compromising the effectiveness of the filtration of the air, which characterizes the present invention. In using the filters of the present invention, typical flow rates of air through the filter range from about 3 to about 30 lpm. The pressure drop across such filters typically is from about 5 to about 60 inches of water, preferably from about 5 to about 25 inches of water. In some applications, the filter may be used together with a pump to assist movement of air across the filter, thereby rendering pressure drop less relevant.

The filters of the present invention include impregnated filters in which the carbon fibers are impregnated with mixtures of materials (e.g., metals) which enhance removal of specific agents (e.g., chemical or biological agents) by the filter.

Particles of iron (e.g., magnetite), molybdenum or silver may be added to the filter structures to enhance their removal of bacteria.

In one embodiment of the present invention, an isotropic pitch precursor is formed such that the resultant fibers define a diameter of approximately 10–25 $\mu$m. The fibers can be in a stabilized, carbonized or activated condition and are cut to an average length of approximately 200 $\mu$m, but that can range from about 100 to about 1,000 $\mu$m. The chopped fibers are then mixed in a water slurry with a binder, such as a phenolic resin. The binder can be any binder known in the art, such as a thermosetting resin adhesive or pitch.

In a preferred forming method, the slurry is transferred to a molding tank (circular) of any cross-section to make cylinders or blocks, or annular to make tubes. The mold has a screen at the bottom. The slurry is filtered through this screen by applying an overpressure of air or applying a vacuum on the drainage side of the screen. In most cases, an acceptable rate of filtration is achieved by relying upon the hydraulic head of slurry. Of course, other molding methods can be utilized (e.g., pressure forming or any of the other various forming methods practiced in the plastics industry).

The resulting green form is partially dried, preferably in air at approximately 50° C. The form is then removed from the mold and the green form is cured (at, for example, 130° C. in air) to produce a cured monolithic body. The resulting composite is then carbonized under an inert gas. Preferably, carbonization is conducted for up to three hours under nitrogen at 650° C. to pyrolize the resin binder.

A composite formed by the above process defines voids or interstitial spaces between the fibers which allow free flow of air through the material and ready access to the carbon fiber surface. Further, the individual carbon fibers are held in place by the pyrolyzed resin binder and thus cannot move or settle due to the flow of air through the material. The carbonized bulk or cured density of the composite material is typically from about 0.2 to about 0.9 g/cc, more preferably from about 0.3 and about 0.55 g/cc.

Following its manufacture, the monolithic carbon fiber composite is activated. Activation of the carbon fibers is accomplished by reaction with steam, carbon dioxide or by chemical activation. The resulting chemical reaction removes carbon and develops pores in the carbon fibers; the pores are classified by their diameter: micropores (less than 20 nm), mesopores (20–50 nm) and macropores (greater than 50 nm).

In a preferred embodiment, the composite is steam activated in a steam/nitrogen atmosphere. The preferred activation conditions are 800–950° C. with the steam at a partial pressure of 0.1–0.9 atmospheres, for a duration of about 1–26 hours, preferably 1–3 hours. The burn-off is calculated from the initial and final weights of the composite. For the present invention, the burn-off is preferably at least about 20%, and further preferably no more than about 80%, most preferably burn-off is in the range from about 40% to about 60%, to provide a composite with good virus, bacteria and parasite removal characteristics in addition to a high capacity for the adsorption of other airborne contaminants. The activation conditions can be varied by changing the activation gas, its concentration, the flow rate, temperature, the furnace configuration and the optional presence of a catalyst to influence total surface area and pore size distribution. Further, the use of a post-activation treatment can be implemented. For example, further heating in a controlled gas atmosphere or the introduction of chemicals could affect the pore size distribution and surface chemistry of the finished composite. Once carbonized or activated, the composite can be machined to any desired shape, forming a monolithic carbon composite.

The composite filters of the present invention are characterized by an extremely open structure. In fact, such filters frequently have a ratio of interstitial area to activated carbon fiber area in their cross-section of from about 3:1 to about 20:1. The result is a porous filter replete with extensive tortuous pathways running through its body. Viruses, bacteria, organics and other contaminants, present at low concentration, must follow these pathways as the air stream passes through the filter. Generally, bacteria are larger than the pores in the activated carbon and it is the open structure (i.e., large interstices/pathways) of the present invention that allows entry of the bacteria inside the composite providing access to the surfaces of the activated carbon fibers that define the boundaries of those interstices/pathways on which the bacteria are effectively trapped. It should also be appreciated that the binder only binds the fibers and particles at the intersection of one fiber with another. Accordingly, most of each fiber's surface pores are maintained accessible for adsorption of organics, viruses and other contaminants. While the viruses are also generally too large to become entrapped in the pores, they do become entrapped on the extensive external carbon fiber surfaces that define the tortuous pathways characteristic of the composite structure. Accordingly, the filtering efficiency provided by the activated carbon fiber composite filters of the present invention is significantly enhanced over any activated carbon filter generally available in the art.

The method of making of the composites is alternatively to mix 100 micron activated carbon fibers with surface areas from 200–2000 $m^2/g$ (burn-offs from 20–75%) with the phenolic resin binder or other binders and water. The ratio of resin to fiber varies from 1:32 to 2:1 preferably 1:16 to 1:4. The slurry is poured into a mold, which is evacuated to remove excess water. The filter cake is ejected and cured at 200° C. for about 3 hours. The composite is then activated in steam for 1–10 hours to activate the resin, or alternatively just carbonized at 800° C. in nitrogen, or yet another alternative is to leave the resin in the cured state.

This method of manufacture results in composites with better structural properties since there is no cracking of the composite due to nonuniform activation throughout the structure. Hence the virus and bacteria removal can be even more efficient than for composites made from nonactivated fibers, which need more activation after manufacture with the possibilities of microcracks appearing.

In another method of making the composites, the fibers and/or particulates are dry mixed with powdered phenolic resin binder (10–15 micron particles). The curing and activation steps are the same as when water is used in the mixture, except that the curing will be faster since there is no release of water.

It should also be appreciated that the present invention comprises methods of removing contaminants from an air stream. While the term "contaminants" as used herein is focused on pathogens, it also includes particulate matter and organic materials (e.g., vapors, odors) which may be present in air. In one aspect, the method comprises passing the air stream, at a flow rate of from about 3 to about 30 lpm, preferably from about 3 to about 20 lpm, through a filter comprising an activated carbon composite, said filter having a density of from about 0.35 to about 0.70 g/cc (preferably from about 0.35 to about 0.50 g/cc, most preferably from about 0.35 to about 0.40 g/cc). The benefit of this method is based on the fact that for a given filter structure, a carbon composite, when compared to a similarly shaped agglomeration of free fibers and particulates, provides cleansing of the air stream at higher flow rates and with a lower pressure drop. In a second embodiment, the method for removing pathogens from an air stream comprises passing the air stream through a filter comprising activated carbon fibers and/or particulates (preferably in the form of a composite), said filter having a density of from about 0.35 to about 0.70 g/cc (preferably from about 0.35 to about 0.50 g/cc, most preferably from about 0.35 to about 0.40 g/cc), such that at least a portion of the air stream (i.e., at least about 50%, preferably at least about 75%) passes through a wall in said filter having a thickness of no greater than about 3 inches (preferably no greater than about 2 inches, more preferably no greater than about 1 inch). The benefit provided by this embodiment of the process is based on the fact that contaminants may be effectively removed from an air stream by passing that stream through a thin wall of the filters of the present invention, thereby allowing a higher flow rate and lower pressure drops than would be required with the more conventional thicker filters of the prior art.

Advantageously, when the carbon fibers are rigidly bonded in a composite monolithic body, there is, during use, little or no movement within the adsorbent bed such as might occur in a bed of granular carbon. Since movement may result in attrition and the production of carbon fines that may pass through the bed and carry contaminants, as well as clog the pores of the bed, the elimination of this movement can be a significant benefit. Further, movement can result in channeling that results in inefficient adsorption. Avoidance of this channeling problem is also a significant benefit of this aspect of the present invention.

In addition to the carbon fiber composites, the filters of the present invention may include, in addition to fibers, carbon particulates and fines, as long as they are bonded together and meet the spacing, void volume and density criteria defined herein. In fact, in certain circumstances, the composites may be made up solely of carbon particulates and fines, as long as they are bonded together and meet the spacing, void volume and density criteria defined herein.

In summary, numerous benefits result from employing the activated carbon composites of the present invention in the air filtration process. A composite filter is provided that is useful for filtering a broad range of contaminants out of an air stream easily, quickly, with high flow rates and with a low pressure drop. The composite filter has a unique open internal structure and a large reactive surface for adsorption which allows for more efficient and rapid removal of contaminants than is attainable with conventional filters of granular activated carbons. This efficient adsorption is achieved in a relatively short contact time and with low pressure energy requirements. Further, no channeling or bypass of contaminants will occur even in a very thin filter bed since the filter is a monolithic body with fibers firmly held or bound in position.

In another embodiment of the present invention, the filter used to remove pathogens from the air stream comprises free activated carbon fibers, rather than a composite structure.

One process for building a free activated carbon fiber filter capable of removing pathogens from an air stream comprises placing activated carbon fibers into a hollow cylinder and applying linear force along the axis of the cylinder, thus compressing the fibers. It is to be understood that the air to be treated is made to flow along the axis of the cylinder which is also the axis of compression. The axial compression described is but one means of compressing fibers and other means of compression may be used including, but not limited to, hydraulic pressure across a membrane, opposed knuckles on a roller pressing against the fibers placed in a hollow form, a levered pressing element, and a hydraulic press. It is to be further understood that the cylinder could as well be any other shape such as a box or a cone which lends itself to axial compression of the fibers. Additionally, the activated carbon fibers can be shaped into an annular shape to take advantage of radial flow (i.e., a candle filter).

Further and optionally, the carbon fibers may be selected from a range of diameters so that when placed together, the interstitial spacing between the first, and larger, diameter fibers will closely conform to the second, and smaller, diameter fibers, and so that the successively smaller diameter fibers will closely conform with the remaining interstitial space between the various selected larger fibers. By this selection of fiber diameters and lengths, the size, form and surface area of the interstitial space can be substantially controlled and made uniform at a smaller scale than would be possible than if a single fiber diameter is used. Additionally, the activated carbon fibers may be combined with other materials, of different shapes, to control interstitial spacing. Such materials may be carbonaceous or non-carbonaceous. Further, the activated carbon fibers may be treated with a bacteriostatic agent, such as closely bound silver or other bacteriostatic means, to prevent bacterial colonies from developing on the activated carbon surfaces. However, to ensure that a filter is serving the function of removing pathogens by size exclusion and/or adsorption per the present invention, as opposed to simply "killing" the pathogens, it is important that the filter be tested without application of chemical agents that provide antibiotic effects.

In one embodiment, the activated carbon filter may be comprised of aligned larger fibers compressed with a plurality of smaller fibers so that the smaller fibers fill in the interstitial space between the larger fibers, forming successively smaller and parallel interstitial spaces along the axis of the fibers and continuous in the axial fiber direction through the entire structure. In this embodiment, it can be seen that the size of the interstitial spaces created is much smaller than the fiber members and uniform through the structure and can readily be controlled by the diameter of the fibers selected.

In addition to air filtration, the filters described herein can be used in air sampler/concentrates apparatus, such as to monitor indoor air quality (including HVAC system monitoring), workplace exposure monitoring, clean room monitoring, infectious disease investigations, biological warfare agent detection.

EXAMPLES

The following examples illustrate the filters and the processes of the present invention. They are intended only to be exemplary and not limiting of the scope of the present invention.

The following describes the procedure used to measure the ability of the carbon filter assemblies of the present invention to filter MS-2 bacteriophage from an aerosol air stream. The removal efficiencies were calculated by comparing the amount of viable MS-2 on reference samples taken upstream and downstream of the carbon filter.

Figure 1:
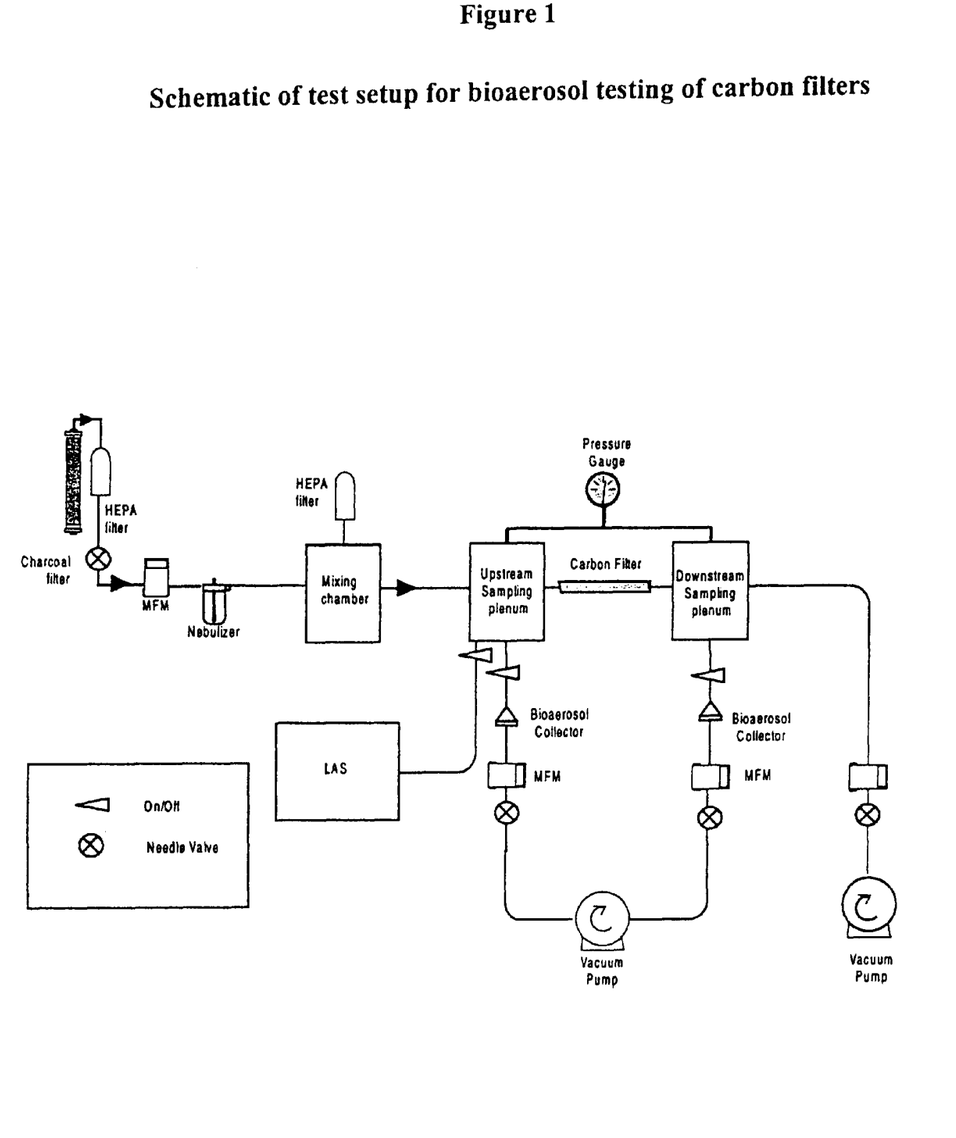
FIG. 1 is a schematic of the test set-up used in the examples.

FIG. 1 is a schematic of the test set-up used. The filter assemblies were connected to the aerosol test system via ¼ inch Swagelock fittings. MS-2 aerosol was generated using a 6-jet Collison nebulizer. The flow rate used for testing of the first three filters was 30 lpm and this was decreased to 10 lpm for the last three filters.

Teflon reference filter samples were collected at 5, 15 and 25 minutes, and each sample was of a five minute duration period. A laser aerosol spectrometer (Particle Measuring Systems, Inc., Boulder, Colo.) was also used to measure the aerosol size distribution. The step-by-step procedure used for the bioaerosol testing is as follows:

Ensure all valves are closed prior to testing of each filter

| | |
|---|---|
| t = −5 min. | Set exhaust pump to give 10 or 30 Lair · min$^{-1}$ |
| | Take 1 minute LAS measurement from upstream port |
| t = 0 | Turn on Collison nebulizer to 15 psi, verify exhaust still at 10 (30) Lair · min$^{-1}$ |
| t = 4:55 | Open upstream and downstream reference filter valves |
| t = 5 | Start pump to pull air through reference filters at 5 l pm, verify exhaust still at 10 (30) Lair · min$^{-1}$ |
| | Take LAS measurement from upstream chamber |
| t = 10 | Stop sample pump and switch out sampling filter holders |
| t = 14:55 | Open reference filter valves |
| t = 15 | Start pump to pull air through reference filters |
| | Take LAS measurement from upstream chamber |
| t = 20 | Stop sample pump and switch out sampling filter holders |
| t = 24:55 | Open reference filter valves |
| t = 25 | Start pump to pull air through reference filters |
| | Take LAS measurement from upstream chamber |
| t = 30 | Stop sample pump |
| t = 31 | Stop Collison nebulizer |
| t = 40 | Turn off exhaust pump |

Remove carbon filter, replace with new carbon filter and repeat procedure.

The Teflon reference filters were analyzed by placing them in a 50 ml conical tube, suspended in 10 ml of phosphate-buffered saline (PBS), and placed on a Wrist Action Shaker (Burrell Scientific, Pittsburgh, Pa.) for 10 minutes. The liquid suspensions were then analyzed for MS-2 according to standard microbiological procedures. This resulted in a quantifiable number of plaque forming units (PFU) for each reference filter. This number was used to determine both the upstream and downstream number of PFU/Lair for each test. The efficiencies for each of the reference filter sets were calculated using the following equation:

$$\text{Efficiency} = 1 - \frac{PFU/Lair \text{ (downstream)}}{FLU/Lair \text{ (upstream)}}$$

The carbon filters tested using this procedure were prepared as follows:

Carbon Filter 1

Activated carbon fibers of approximately 200 micron length (Anshan Carbon Fibers, P-200) were packed into a bed with a fiber density of 0.37 g/cc. The fibers were received in the carbonized form and activated at 877° C. for 3 hours. The burn-off during activation was 45%. The BET surface area of the material is 1202 m$^2$/g. An adsorption column was made up by packing the fibers into a PVC reactor of 1.045 inches diameter and 3.0 inches long. The weight of fibers was 14.8 g. The density of the activated carbon fiber bed was 0.367 g/cc. A 8 micron glass filter paper was put at the end of the reactor to prevent carbon fines to be carried out from the reactor.

The column was tested for MS-2 bacteriophage adsorption at a high flow rate of 30 lpm (44690 column volumes/hr) of air spiked with 2.0×10$^5$ PFU/ml of MS-2. The removal of MS-2 was better than 99% (99.3%) for 5 min, then 3 logs (99.9%) after 15 minutes. It improved to 4 logs (99.995%) after 25 minutes. The adsorption was stopped after 25 minutes before saturation was reached. Detailed results and conditions of the virus adsorption test are shown for Example 1 in Table 1.

Carbon Filter 2

Activated carbon fibers of approximately 200 micron length (Anshan Carbon Fibers, P-200) were packed into a bed with a fiber density of 0.37 g/cc. The fibers were received in the carbonized form and activated at 877° C. for 3 hours. The burn-off during activation was 46%. The BET surface area of the material is 1220 m$^2$/g. An adsorption column was made up by packing the fibers into a PVC reactor of 1.045 inches diameter and 2.0 inches long. The weight of fibers was 10.3 g. The density of the fiber bed was 0.370 g/cc. 0.2 g of P-800 fibers were put at the end of the reactor to prevent clogging of the 20 micron glass filter paper at the end of the reactor to prevent carbon fines from exciting the reactor.

The column was tested for MS-2 bacteriophage adsorption at a high flow rate of 10 lpm (23321 column volumes/hr) of air spiked with 2.0×10$^5$ PFU/ml of MS-2. The removal of MS-2 was better than 3 logs (99.9%) for 5 min, then 3 logs (99.9%) after 15 minutes. It was still 3 logs (99.96%) after 25 minutes. The adsorption was stopped after 25 minutes before saturation was reached. Detailed results and conditions of the virus adsorption test are shown in Table 1.

Carbon Filter 3

Activated carbon fibers of approximately 200 micron length (Anshan Carbon Fibers, P-200) were packed into a bed with a fiber density of 0.37 g/cc. The fibers were received in the carbonized form and activated at 877° C. for 3 hours. The burn-off during activation was 46%. The BET surface area of the material is 1220 m$^2$/g. An adsorption column was made up by packing the fibers into a PVC reactor of 1.045 inches diameter and 3.0 inches long. The weight of fibers was 10.7 g. The density of the fiber bed was 0.370 g/cc. 1.19 g of multiwalled carbon nanotubes (MWNT) were put at the end of the reactor. A micron glass filter paper was placed at the end of the reactor to prevent carbon fines from exciting the reactor.

The column was tested for MS-2 bacteriophage adsorption at a high flow rate of 30 lpm (44690 column volumes/hr) of air spiked with 2.0×10$^5$ PFU/ml of MS-2. The removal of MS-2 was 82.6% for 5 min, then 2 logs (99.8%) after 15 minutes. And 99.6% after 25 minutes. The adsorption was stopped after 25 minutes before saturation was reached. Detailed results and conditions of the virus adsorption test are shown for carbon filter 3 in Table 1.

Carbon Filter 4

The production method for this material which was made directly as a 1 in. diameter, 4 in. long column involved mixing 28 g of P200 pitch-based carbon fibers (R303T) with 120 cc of water and 7 g of Durez 2-step phenolic resin. After mixing, the slurry was poured into a mold made from a 1 in. ID PVC tube, where the fiber-resin mixture adapts to the mold shape. The mixture was allowed to settle for 10 seconds before applying a vacuum for 1 min. to draw the remaining water through the cake and effect partial drying. The composite was ejected from the mold, and cured at 200° C. for 3 hours.

The cured composite was then activated in steam at 850° C. for 4.5 hours at a nitrogen flow rate of 2 lpm and a water flow rate of 100 cc/hour. The burn-off was 41%. The BET surface area of the material was 1130 m$^2$/g. The density of material was 0.324 g/cc.

An adsorption column was made up from the 2.045 in. long, 0.953 in. diameter sample. The weight of the sample was 8.0 g. The column was tested for MS-2 bacteriophage adsorption at a high flow rate of 10 lpm (23321 column volumes/hr) of air spiked with 2.0×10$^5$ PFU/ml of MS-2. The removal of MS-2 was better than 3 logs (99.9%) for 5 min, then 3 logs (99.9%) after 15 minutes. It was still 3 logs (99.96%) after 25 minutes. The adsorption was stopped after 25 minutes before saturation was reached. Detailed results and conditions of the virus adsorption test are shown in Table 1.

Carbon Filter 5

The production method for this sample is similar to that for Example 4. It was made from 28 g of P200 pitch-based carbon fibers (R303T), 120 cc of water and 7 g of Durez 2-step phenolic resin.

The cured composite was then activated in steam at 877° C. for 3.5 hours at a nitrogen flow rate of 2 lpm and a water flow rate of 100 cc/hour. The burn-off was 41%. The BET surface area of the material was 1130 m$^2$/g. The density of material was 0.364 g/cc.

An adsorption column was made up from the 3.03 in. long, 0.949 in. diameter sample. The weight of the sample was 12.2 g. The column was tested for MS-2 bacteriophage adsorption at a high flow rate of 30 lpm (44690 column volumes/hr) of air spiked with 2.0×10$^5$ PFU/ml of MS-2. The removal of MS-2 was 99.2% for 5 min, then 1 log (94.3%) after 15 minutes, and 97.8% after 25 minutes. The adsorption was stopped after 25 minutes before saturation was reached. Detailed results and conditions of the virus adsorption test are shown for carbon filter 3 in Table 1.

Carbon Filter 6

The production method for this sample is similar to that for Example 4. It was made from 28 g of P200 pitch-based carbon fibers (R303T), 120 cc of water and 7 g of Durez 2-step phenolic resin.

The cured composite was then activated in steam at 877° C. for 3.5 hours at a nitrogen flow rate of 2 lpm and a water flow rate of 100 cc/hour. The burn-off was 41%. The BET surface area of the material was 1130 m$^2$/g. The density of material was 0.346 g/cc.

An adsorption column was made up from the 2.04 in. long, 0.960 in. diameter sample. The weight of the sample was 8.1 g. The column was tested for MS-2 bacteriophage adsorption at a high flow rate of 10 lpm (23321 column volumes/hr) of air spiked with 2.0×10$^5$ PFU/ml of MS-2. The removal of MS-2 was better than 3 logs (99.9%) for 5 min, then 3 logs (99.9%) after 15 minutes. It was still 3 logs (99.96%) after 25 minutes. The adsorption was stopped after 25 minutes before saturation was reached. Detailed results and conditions of the virus adsorption test are shown in Table 1.

Carbon Filter 7

The production method for this sample is similar to that for Example 4. It was made from 28 g of P100 pitch-based carbon fibers (R303T), 120 cc of water and 7 g of Durez, 2-step phenolic resin.

The cured composite was then activated in steam at 877° C. for 3.5 hours at a nitrogen flow rate of 2 lpm and a water flow rate of 100 cc/hour. The burn-off was 53%. The density of material was 0.375 g/cc.

An adsorption column was made up from the 1.98 in. long, 1.81 in. diameter sample. The weight of the sample was 31.25 g. The volume of the column was 83.3 cc. The column was tested for MS-2 bacteriophage adsorption at a flow rate of 3 lpm (36 column volumes/min or 2161 column volumes/hr) of air spiked with 1.9×10$^6$ PFU/ml of MS-2 for the first 15 minutes, then 1.6×10$^5$ PFU/ml for the next ten, then 1.3×10$^5$ PFU/ml for the last ten minutes. The removal of MS-2 was better than 4 logs (99.99%) for the first 10 min, then 3 logs (99.9%) after 15 minutes. It was still 3 logs (99.96%) after 25 minutes. The adsorption was stopped after 25 minutes before saturation was reached. The pressure drop during this experiment was 13" H$_2$O for a flow rate of 3 lpm.

Detailed results and conditions of the virus adsorption test are shown in Table 1.

Carbon Filter 8

The production method for this sample is similar to that for Example 4. It was made from 28 g of P100 pitch-based carbon fibers (R303T), 120 cc of water and 7 g of Durez 2-step phenolic resin.

The cured composite was then activated in steam at 877° C. for 3.5 hours at a nitrogen flow rate of 2 lpm and a water flow rate of 100 cc/hour. The burn-off was 52%. The density of material was 0.375 g/cc.

An adsorption column was made up from a 1.0 in. tall, 1.82 in. diameter sample. The weight of the sample was 15.63 g. The volume of the column was 41.7 cc. The column was tested for MS-2 bacteriophage adsorption at a flow rate of 3 lpm (72 column volumes/min or 4320 column volumes/hr) of air spiked with 5.4×10$^5$ PFU/ml of MS-2 for the first 15 minutes, then $1.6 \times 10^6$ PFU/ml for the next ten, then $2.6 \times 10^6$ for the last ten minutes. The removal of MS-2 was better than 4 logs (99.99%) after 10, 20 and 30 minutes. The adsorption was stopped after 30 minutes before saturation was reached. The pressure drop during this experiment was 10" $H_2O$ for a flow rate of 3 lpm. Detailed results of the virus adsorption test are shown in Table 1.

Carbon Filter 9

P-200 carbon fibers were activated in steam at 877° C. for 3.5 hours at a nitrogen flow rate of 2 lpm and a water flow rate of 100 cc/hour. The burn-off was 40%.

The volume of the column was 27.84 cc. The density of the packed bed was 0.392 g/cc. The column was tested for MS-2 bacteriophage adsorption at a flow rate of 3 lpm (72 column volumes/min or 4320 column volumes/hr) of air spiked with $5.4 \times 10^5$ PFU/ml of MS-2 for the first 15 minutes, then $1.6 \times 10^6$ PFU/ml for the next ten, then $2.6 \times 10^6$ for the last ten minutes. The removal of MS-2 was better than 4 logs (99.99%) after 10, 20 and 30 minutes. The adsorption was stopped after 30 minutes before saturation was reached. The pressure drop during this experiment was 24" $H_2O$ for a flow rate of 3 lpm. Detailed results of the virus adsorption test are shown in Table 1.

TABLE 1

Results of Virus Adsorption Test

| Carbon Filter ID | Type | Bed Depth (cm) | Bed Diam. (cm) | Dens (g/cc) | Air Flow Rate Through Filter (Lair/min) | Linear Air Flow Through Filter (Lair/min cm2) | Pressure drop ("H2O) | Upstream Concentration (PFU* Lair-1) | Downstream Concentration (PFU* Lair-1) | MS-2 Removal Efficiency (%) |
|---|---|---|---|---|---|---|---|---|---|---|
| 3 | fiber | 3.00 | 1.05 | 0.37 | 30 | 5.9 | 42 | 6.9E+03 | 1.2E+03 | 82.6 |
|   |   |   |   |   |   |   |   | 2.1E+05 | 4.7E+02 | 99.8 |
|   |   |   |   |   |   |   |   | 2.4E+05 | 8.9E+02 | 99.6 |
| 5 | comp | 3.03 | 0.95 | 0.36 | 30 | 5.9 | 42 | 2.8E+05 | 2.4E+03 | 99.2 |
|   |   |   |   |   |   |   |   | 1.6E+05 | 9.2E+03 | 94.3 |
|   |   |   |   |   |   |   |   | 2.9E+05 | 6.4E+03 | 97.8 |
| 1 | fiber | 3.00 | 1.05 | 0.37 | 30 | 5.9 | 41 | 2.0E+05 | 1.4E+05 | 99.3 |
|   |   |   |   |   |   |   |   | 2.1E+05 | 2.3E+02 | 99.9 |
|   |   |   |   |   |   |   |   | 1.9E+05 | <1.0E+01 | 99.995 |
| 2 | fiber | 2.00 | 1.05 | 0.37 | 10 | 2 | 6 | 1.4E+05 | 1.5E+02 | 99.9 |
|   |   |   |   |   |   |   |   | 2.7E+05 | 1.8E+02 | 99.9 |
|   |   |   |   |   |   |   |   | 1.0E+05 | 4.0E+01 | 99.96 |
| 6 | fiber | 2.04 | 0.96 | 0.35 | 10 | 2 | 6 | 2.4E+05 | 3.7E+02 | 99.8 |
|   |   |   |   |   |   |   |   | 2.4E+05 | 1.1E+03 | 99.5 |
|   |   |   |   |   |   |   |   | 3.3E+05 | 8.5E+02 | 99.7 |
| 4 | comp | 2.05 | 0.95 | 0.32 | 10 | 2 | 5 | 2.7E+05 | 1.2E+03 | 99.6 |
|   |   |   |   |   |   |   |   | 3.1E+05 | 1.1E+03 | 99.7 |
|   |   |   |   |   |   |   |   | 2.4E+05 | <1.0E+01 | 99.996 |
| 7 | comp | 2.00 | 2.00 | 0.38 | 3 | 0.2 | 13 | 1.90E+06 | 5.00E+01 | 99.9974 |
|   |   |   |   |   |   |   |   | 1.56E+05 | 5.00E+01 | 99.9679 |
|   |   |   |   |   |   |   |   | 1.30E+05 | 5.00E+01 | 99.9615 |
| 8 | comp | 1.00 | 2.00 | 0.38 | 3 | 0.2 | 10 | 5.40E+05 | 5.00E+01 | 99.9907 |
|   |   |   |   |   |   |   |   | 1.64E+06 | 5.00E+01 | 99.997 |
|   |   |   |   |   |   |   |   | 2.60E+06 | 5.00E+01 | 99.9981 |
| 9 | fiber | 2.00 | 1.00 | 0.22 | 3 | 0.6 | 24 | 8.20E+05 | 5.00E+01 | 99.9939 |
|   |   |   |   |   |   |   |   | 2.90E+06 | 5.00E+01 | 99.9983 |
|   |   |   |   |   |   |   |   | 9.40E+06 | 5.00E+01 | 99.9995 |
| 10 | fiber | 2.00 | 1.00 | 0.70 | 3 | 0.6 | 59 | 3.00E+06 | 5.00E+01 | 99.9983 |
|   |   |   |   |   |   |   |   | 1.18E+07 | 5.00E+01 | 99.9996 |
|   |   |   |   |   |   |   |   | 4.00E+06 | 5.00E+01 |   |

CINlibrary/1090019.1/243-395625

An adsorption column was made up from a 2.0 in. tall, 1.82 in. diameter sample. The weight of the sample was 5.06 g. The volume of the column was 22.9 cc. The column was tested for MS-2 bacteriophage adsorption at a flow rate of 3 lpm (72 column volumes/min or 4320 column volumes/hr) of air spiked with $5.4 \times 10^5$ PFU/ml of MS-2 for the first 15 minutes, then $1.6 \times 10^6$ PFU/ml for the next ten, then $2.6 \times 10^6$ for the last ten minutes. The removal of MS-2 was better than 4 logs (99.99%) after 10, 20 and 30 minutes. The adsorption was stopped after 30 minutes before saturation was reached. The pressure drop during this experiment was 24" $H_2O$ for a flow rate of 3 lpm. Detailed results of the virus adsorption test are shown in Table 1.

Carbon Filter 10

P-200 carbon fibers were activated in steam at 877° C. for 3.5 hours at a nitrogen flow rate of 2 lpm and a water flow rate of 100 cc/hour. The burn-off was 29.9%.

An adsorption column was made up from a 2.0 in. tall, 1.0 in. diameter sample. The weight of the sample was 19.5 g.

What is claimed is:

1. A process for removing pathogens from air, comprising passing said air, at a flow rate of from about 3 to about 30 lpm, through a filter comprising activated carbon fibers, said filter having a density of from about 0.35 to about 0.70 g/cm³, and at least one wall having a thickness no greater than about 3 inches through which at least a portion of the air passes during use.

2. The process according to claim 1 wherein the filter has a VRI of at least about 99%.

3. The process according to claim 2 wherein the filter has a VRI of at least about 99.9%.

4. The process according to claim 3 wherein the filter has a VRI of at least about 99.99%.

5. The process according to claim 3 wherein the filter has a void volume of from about 63% to about 95%, and a mean inter-fiber spacing of at least about 30 μm.

6. The process according to claim 5 wherein the filter has a void volume of from about 71% to about 81%, and a mean inter-fiber spacing of from about 42 μm to about 73 μm.

7. The process according to claim 5 wherein the burn-off during activation of the filter is at least about 20%.

8. The process according to claim 7 wherein the burn-off during activation of the filter is up to about 70%.

9. The process according to claim 8 wherein the burn-off during activation of the filter is from about 40% to about 50%.

10. The process according to claim 8 wherein the filter has a micropore volume of from about 0.2 to about 0.9 cc/g, and a BET surface area of from about 500 to about 3,000 m²g.

11. The process according to claim 8 wherein the filter has a shape selected from disc, annular/candle, corrugated and block.

12. The process according to claim 11 wherein the flow path of the air through the composite portion of the filter is no greater than about 2 inches.

13. The process according to claim 8 wherein the flow rate is from about 3 to about 20 lpm.

14. The process according to claim 8 wherein the filter has a density of from about 0.35 to about 0.50 g/cm³.

15. The process according to claim 8 wherein the filter can be disinfected and regenerated on-line by heating the composite for a short period of time above about 120° C.

16. The process according to claim 15 wherein the heating is accomplished by applying an electric current through the composite.

17. The process according to claim 8 wherein the filter is comprised of carbon fibers, carbon particulates and a binder to obtain properties amenable to virus removal.

18. A process for removing pathogens from air, comprising passing said air through a filter comprising activated carbon fibers, said filter having a density of from about 0.35 to about 0.70 g/cm³, such that at least a portion of the air passes through a wall in said filter having a thickness of no greater than about 3 inches.

19. The process according to claim 18 wherein the filter is a carbon fiber composite filter.

20. The process according to claim 19 wherein the filter has a VRI of at least about 99%.

21. The process according to claim 20 wherein the filter has a VRI of at least about 99.9%.

22. The process according to claim 21 wherein the filter has a void volume of from about 63 to about 95%, and a mean inter-fiber spacing of from about 30 $\mu$m to about 302 $\mu$m.

23. The process according to claim 22 wherein the filter has a void volume of from about 71% to about 81%, and a mean inter-fiber spacing of from about 42 $\mu$m to about 73 $\mu$m.

24. The process according to claim 22 wherein the burn-off during activation of the filter is at least about 20%.

25. The process according to claim 24 wherein the burn-off during activation of the filter is no greater than about 80%.

26. The process according to claim 25 wherein the burn-off during activation of the filter is from about 40% to about 60%.

27. The process according to claim 25 wherein the filter has a micropore volume of from about 0.3 to about 0.8 cc/g, and a BET surface area of from about 800 to about 1,600 m²/g.

28. The process according to claim 25 wherein the filter has a shape selected from disc, candle/annular, corrugated and block.

29. The process according to claim 28 wherein said wall has a thickness of no greater than about 2 inches.

30. The process according to claim 25 wherein the flow rate of the air is from about 3 to about 20 L/m.

31. The process according to claim 25 wherein the filter has a density of from about 0.35 to about 0.50 g/cm³.

32. The process according to claim 29 wherein said wall has a thickness of no greater than about 1 inch.

33. The process according to claim 18 wherein the filter can be disinfected and regenerated on-line by heating the composite for a short period of time above about 60° C.

34. The process according to claim 33 wherein the heating is accomplished by applying an electric current through the composite.

* * * * *